United States Patent [19]
Salk et al.

[11] Patent Number: 5,885,578
[45] Date of Patent: Mar. 23, 1999

[54] PREVENTION AND TREATMENT OF RETROVIRAL DISEASE

[75] Inventors: Jonas Salk, La Jolla; Dennis J. Carlo, Rancho Santa Fe, both of Calif.

[73] Assignee: The Immune Response Corporation, Carlsbad, Calif.

[21] Appl. No.: 469,739

[22] Filed: Jun. 5, 1995

Related U.S. Application Data

[62] Division of Ser. No. 233,508, Apr. 26, 1994, abandoned, which is a continuation of Ser. No. 121,318, Sep. 15, 1993, abandoned, which is a continuation of Ser. No. 975,899, Nov. 10, 1992, Pat. No. 5,256,767, which is a continuation of Ser. No. 200,752, May 31, 1988, abandoned, which is a continuation-in-part of Ser. No. 60,280, Jun. 10, 1987, abandoned.

[51] Int. Cl.$^6$ .............................. C12N 7/00; A61K 39/21; A61K 39/12; C07K 1/00
[52] U.S. Cl. .................................. 424/188.1; 424/204.1; 424/208.1; 424/184.1; 530/350; 435/235.1
[58] Field of Search ....................... 435/235.1; 530/350, 530/388.35, 388.3; 424/188.1, 204.1, 184.1

[56] References Cited

U.S. PATENT DOCUMENTS

| | | | |
|---|---|---|---|
| 4,086,134 | 4/1978 | Jarrett | 195/1.2 |
| 4,591,505 | 5/1986 | Prince | 424/101 |
| 4,663,436 | 5/1987 | Elder et al. | 530/324 |
| 4,716,102 | 12/1987 | Levy | 435/5 |

FOREIGN PATENT DOCUMENTS

| | | |
|---|---|---|
| 187/041 | 7/1986 | European Pat. Off. . |
| 199301 | 10/1986 | European Pat. Off. . |
| 250 128 | 12/1987 | European Pat. Off. . |
| WO86/02930 | 5/1986 | WIPO . |
| WO 86/06099 | 10/1986 | WIPO . |
| WO 87/02892 | 5/1987 | WIPO . |
| WO88/07058 | 9/1988 | WIPO . |
| 93250368.3 | 2/1994 | WIPO . |

OTHER PUBLICATIONS

Fox, 1994, "No winners against AIDS", Biotechnology 12:128.
Cohen, 1993, "Jitters Jeopardize AIDS . . . " Science 262:980–981.
Baum, "The search for vaccines," Chem. & Engr. News 65:27–34 (1987).
Cease et al., "Helper T–cell antigenic site identification in the acquired immunodeficiency syndrome virus gp120 envelope protein and induction of immunity in mice to the native protein using a 16–residue synthetic peptide," Proc. Natl. Acad. Sci. 84:4249–4253 (1987).
Chan et al., "Induction of anti–HIV neutralizing antibodies by synthetic peptides," The EMBO Journal 5:3065–3071 (1986).
Chang et al., Nature 315:151–154 (1985).
Defendi et al., "Oncogenicity by DNA Tumor Virsues: Enhancement after Ultraviolet and Cobalt–60 Radiations," Science 157:703–705 (1967).
Fauci, Proc. Natl. Acad. Sci. USA 83:9278–9283 (1986).

Fischer, "Therapeutic Uses of Intravenous Gammaglobulin for Pediatric Infections," Pediatric Clinics of North America 35:517–533 (1988).
Kennedy et al., "Perspective on Developing Anti–idiotyp–based Vaccines for Controlling HIV Infection," Gower Acad. J. Ltd., AIDS 1988 2:s119–s127 (1988).
Kennedy et al., "Anti–Idiotypic Antibody Vaccines for Type B Viral Hepatitis in Chimpanzees," Science 232:220–223 (1986).
Koff et al., Science 241:426–432 (1988).
Kramer et al., Science 231:1580–1584 (1986).
Larue et al., "Suitable hollow fiber immunobioreactors for specific ex vivo removal of antibodies and antigens from plasma" Chem. Abstracts vol. 103, No. 25, Dec. 23, 1985, abstract No. 212882j.
Marx et al., "Prevention of Simian Acquired Immune Deficiency Syndrome with a Formalin–Inactivated Type D Retrovirus Vaccine," J. of Virology 60:431–435 (1986).
Marx, "Problems with AIDS Vaccines," Science 228:162–165 (1985).
McClelland et al., "Clinical Use of Immunoglobulins," Clinics In Haematology 13:39–69 (1984).
Newmark, "Problems with AIDS Vaccines," Nature 324:304–305 (1986).
Quinnan et al., Transfusion 26 (3):481–483 (1986).
Reed et al., J. Cell. Biochem. Suppl. 10A, p. 224, Abs. #D1131 (Jan.–Feb. 1986).
Robert–Guroff et al., "In Vitro Generation of an HTLV–III Variant by Neutralizing Antibody," J. of Immunology 137:3306–3309 (1986).
Salk, Nature 327:473–476 (1987).
Sarngadharan, Cancer Res. (Supplemental) 45:4574–4577 (1985).
Sternberg et al., "Predicition of antigenic determinants and secondary structures of the major AIDS virus proteins," FEBS Letters 218:231–237 (1987).
Stiehm, "Standard and Special Human Immune Serum Globulins as Therapeutic Agents," Pediatrics 63:301–319 (1979).
Zagury et al., Nature 326:249–250 (1987).

Primary Examiner—Lynette F. Smith
Attorney, Agent, or Firm—Campbell & Flores LLP

[57] ABSTRACT

The present invention provides a non-infectious immunotherapeutic containing retroviral particles devoid of outer envelope proteins or containing selected antigens isolated from a retrovirus. There is also provided a vaccine effective against HIV. In one aspect, the immunogen is useful for immunizing an individual previously infected by a retrovirus including HIV, so as to induce immunoprotective factors protective against progression of the infection. In another aspect, the vaccine is useful for vaccinating an individual not previously infected with HIV in order to prevent subsequently acquired infection. In another aspect, there is provided a method of rendering a viral immunogen non-infectious. The immunogen may also be used to produce antibodies for passive immunotherapy, alone or in conjunction with active immunotherapy, in individuals infected with a retrovirus, including HIV, preferably those individuals exhibiting low levels of antibodies to retroviral gene products other than the outer envelope.

14 Claims, 4 Drawing Sheets

PREVENTION AND TREATMENT OF RETROVIRAL DISEASE

BACKGROUND OF THE INVENTION

This application is a divisional of U.S. patent application Ser. No. 08/233,508, filed Apr. 26, 1994, abandoned, which is a continuation of Ser. No. 08/121,318, filed Sep. 15, 1993, now abandoned, which is a continuation of Ser. No. 07/975,899, filed Nov. 10, 1992, issued as U.S. Pat. No. 5,256,767, which is a continuation of Ser. No. 07/200,752, filed May 31, 1988, now abandoned, which is a continuation-in-part of United States Patent application Ser. No. 060,280, filed Jun. 10, 1987, now abandoned, the entire specification of which is incorporated herein by reference.

This invention relates generally to agents and methods for the prevention and treatment of retroviral disease and more specifically to an outer envelope free viral preparation for use in vaccination against and immunotherapy of Human Immunodeficiency Virus.

Acquired Immune Deficiency Syndrome, also known as AIDS, has been described as a modern plague. In the seven years since its first description in 1981, it has claimed almost 60,000 victims, and accounted for over 32,000 deaths in the United States alone. However, the true impact of the disease has yet to be felt. The virus may remain latent in infected individuals for five or more years before symptoms appear. Many Americans may unknowingly be infected and capable of infecting others who might come into contact with their body fluids. Thus, if unchecked, the personal, social and economic impact of AIDS will be enormous.

The causative agent of AIDS is the retrovirus Human Immunodeficiency Virus (HIV). Retroviruses are distinguished by the fact that their genetic material, which is RNA, encodes the information for viral replication. Upon infection of a host cell, it acts as a template for the transcription to DNA, catalyzed by an enzyme called reverse transcriptase. The DNA so produced enters the cell nucleus where it is integrated into the host DNA as a provirus. When properly activated, the retroviral-derived DNA is transcribed and translated to produce RNA containing virions which are then released from the cell by a budding process.

Certain viruses, including retroviruses, may remain in a latent state for months or years before they are activated and virions are produced. Although asymptomatic, a host may nonetheless harbor the virus in a proviral form, thus being potentially at risk of disease and of infecting others.

When an individual becomes infected with HIV, the virus preferentially attaches to and enters a particular class of cells termed T4 lymphocytes, characterized by the presence of a cell surface marker termed CD4. These white blood cells play an integral role in the immune system, functioning as critical components of both the humoral and cellular immune response. Much of the deleterious effect of HIV can be attributed to the functional depression or destruction of T4 lymphocytes.

The intact HIV virion is roughly spherical and is approximately 110 nm in diameter. The virion has an outer membrane covered with knobs or spikes made up of glycoprotein, gp160/120. In addition, there exists a transmembrane protein termed gp41. Inside the virion are two structural proteins: an outer shell composed of the phosphoprotein p17 and an inner nucleoid or central core made up of the phosphoprotein, p24. The viral RNA is present inside the core along with two copies of the reverse transcriptase enzyme, p66/51, which is necessary for the synthesis of viral DNA from the RNA template. A schematic model of HIV is presented in FIG. 1.

As shown in FIG. 2, the HIV RNA genome encodes three major structural genes: gag, pol and env, which are flanked at either end by long terminal repeat (LTR) sequences. The gag gene codes for the group-specific core proteins, p55, p39, p24, p17 and p15. The pol genes code for the reverse transcriptase p66/p51 and the protease p31. The env genes encode the outer envelope glycoprotein gpl20 and its precursor gpl60 and the transmembrane glycoprotein gp41. Some of the genes tend to be highly variable, particularly the env genes. In addition, there are five other genes, not shared by other retroviruses, which are either involved in transcriptional or translational regulation or encode other structural proteins. The entire HIV genome has now been sequenced. See Ratner et al. Nature 313:277 (1985) which is incorporated herein by reference.

The HIV attaches to host cells by an interaction of the envelope glycoproteins with a cell surface receptor. It appears that when HIV makes contact with a T4 cell, gpl20 interacts with the CD4 receptor. The viral envelope is then fused with the cell membrane and the inner core of the virus enters the infected cell where the transcription of RNA into a DNA provirus is catalyzed by reverse transcriptase. The provirus may remain in the cell in a latent form for some months or years, during which time the infected individual is asymptomatic. However, if the virus is later activated causing viral replication and immunosuppression the individual will then be susceptible to the opportunistic infections, including cancer, associated with AIDS. Other human retroviruses have outer envelope proteins.

As yet, no vaccine or treatment is known which is effective against the AIDS syndrome. Attempts to develop vaccines have thus far failed. Certain antibodies reactive with HIV, notably anti-gpl60/120 and virus neutralizing antibodies, are present at high levels throughout both the asymptomatic and symptomatic phases of the HIV infection, suggesting that rather than playing a protective role, such antibodies may in fact promote the attachment and penetration of the virus into the host cell.

There thus exists a need for effective agents to be used in the prevention and therapy of retroviral infections, particularly those attributed to HIV. The present invention satisfies these needs and provides related advantages as well.

SUMMARY OF THE INVENTION

The present invention provides a non-infectious immunogen containing retroviral particles free of outer envelope proteins or containing selected antigens isolated from a retrovirus. In one aspect, the immunogen is useful for immunizing an individual infected by a retrovirus including HIV, so as to induce immunoprotective factors protective against progression of the infection. In another aspect, the immunogen is useful for vaccinating an individual not previously infected with HIV in order to prevent subsequent infection. In another aspect, there is provided a method for rendering a viral immunogen non-infectious. The immunogen may also be used to produce antibodies for passive immunotherapy, alone or in conjunction with active immunotherapy, in individuals infected with a retrovirus, including HIV.

DETAILED DESCRIPTION OF THE INVENTION

This application is a continuation-in-part of U.S. patent application Ser. No. 060,280, filed Jun. 10, 1987, the entire specification of which is incorporated herein by reference.

The invention provides an effective means for the prevention of HIV infection and subsequent HIV caused AIDS Related Complex (ARC) and AIDS and for the post-exposure treatment for arresting progression of retroviral infections including HIV. Individuals who have been exposed to the HIV virus express in their serum certain antibodies specific for HIV. Such individuals are termed "seropositive" for HIV, in contrast to individuals who are "seronegative." The presence of HIV specific antibodies can be determined by commercially available assay systems. The level of these antibodies is indicative of the progression of the AIDS syndrome.

Figure 3:
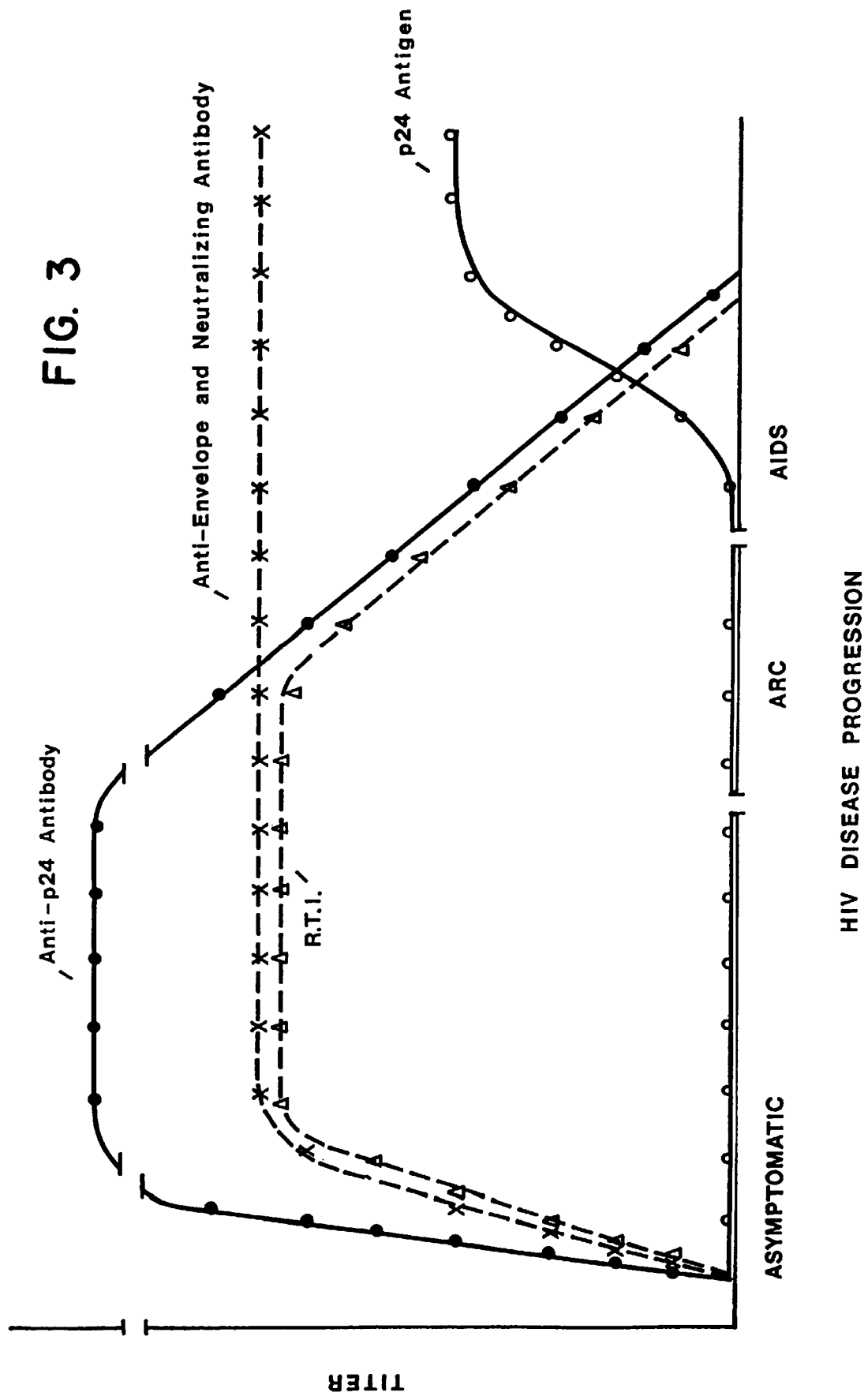
FIG. 3 provides a schematic representation of the level of certain HIV antibodies and antigens present at various time in the progression of the HIV infection to AIDS.

As shown schematically in FIG. 3, high levels of anti-gp160/120 (outer envelope) antibody, which are present in the asymptomatic phase of the HIV infection also persist in the symptomatic phase. The level of anti-p24 antibody in the asymptomatic phase is high but appears to decline in the symptomatic phase. Similarly, HIV seropositive sera contain an antibody that inhibits the function of reverse transcriptase (anti-RT antibody or RTI). In individuals in whom RTI is present at high levels, attempts at virus isolation are less frequently positive than in those in whom it is absent. It therefore appears that the decline of cellular and humoral immunoprotective factors such as $T_4$ cells and anti-GAG antibodies, including anti-p24, and anti-POL antibodies, including RTI, is associated with progression of the HIV infection to AIDS.

The production of immunoprotective factors may be induced by vaccinating an individual with an effective immunogen. In the past, attempts have been made to develop a vaccine based on certain viral proteins, for example the envelope proteins. The present invention relates to an immunogen containing HIV gene products excluding the outer envelope proteins which is useful in stimulating the production of immunoprotective factors effective for preventing infection in non-infected individuals and for slowing or preventing the progression of the HIV infection to AIDS in infected individuals. The immunogen comprises intact viral particles from which the outer envelope has been removed, or comprises one or more HIV gene products other than gp120 or gp160.

A. Definitions

As used herein, the term "retrovirus" refers to a virus having as its genetic material ribonucleic acid (RNA) which is transcribed into DNA which is inserted into the host genome. Examples of retroviruses include HTLV-I, HTLV-II STLV-I, and the lentivirus family including HIV, visna virus, equine infectious anemia virus, feline immunodeficiency virus and bovine immunodeficiency virus. These are described in Fauci, Science 239:617 (1988), and references included therein, each of which are incorporated herein by reference.

As used herein, the term "HIV" includes types 1 and 2 and is synonymous with HTLV-III and LAV-1 and LAV-2. HIV refers to the virus generically and includes all forms, subtypes and variations. Various cell lines permanently infected with the HIV virus have been developed and deposited with the ATCC including those having accession numbers CCL 214, TIB 161, CRL 1552 and CRL 8543, all of which are described in U.S. Pat No. 4,725,669 and Gallo, Scientific American 256:46 (1987) each of which are incorporated herein by reference.

As used herein, the term "outer envelope protein" refers to that portion of the membrane glycoprotein of a retrovirus which protrudes beyond the membrane, as opposed to the transmembrane protein, gp41. The outer envelope protein is, in HIV, synonymous with gp120 and its precursor gp160.

As used herein, the term "outer envelope free" refers to a preparation of retroviral particles or retroviral gene products devoid of the outer envelope proteins.

As used herein, the term "gp120" or "gp160/120" refers to glycoproteins having either the antigenic specificity or the biological function of the outer envelope protein; gp160 is believed to be the precursor of gp120.

As used herein, "AIDS" refers to Acquired Immune Deficiency Syndrome as described by Adler, Brit. Med. J. 294:1145 (1987). It is characterized by tumors and a series of opportunistic infections. "ARC" refers to AIDS-Related Complex as described by Adler, Sunra. The symptomatic phase of HIV infection refers to the onset of symptoms characteristic of ARC or AIDS. The "AIDS syndrome" includes both AIDS and ARC.

As used herein, the term "gene product" refers to a polypeptide or protein which is encoded by a gene. The term is intended to include protein derivatives such as glycoproteins. It is understood that limited modifications may be made in the amino acid sequence of the gene product without destroying the biological function or immunogenicity of the gene product and that only a portion of the primary sequence may be required for immunogenicity.

As used herein, the term HIV infected or HIV non-infected refer to humans in whom the HIV virus or provirus is present, or is not present, respectively. Retrovirus infected or retrovirus non-infected refer to individuals in whom a retrovirus or provirus is present, or is not present, respectively. At the present time, serological tests to detect the presence of antibodies to the virus are the most widely used method of determining infection. Such methods can, however, result in both false negatives, as where an individual has contracted the virus but not yet mounted an immune response, and in false positives, as where a fetus may acquire the antibodies, but not the virus from the mother. Other methods of determining the presence of the virus have or may become available. Where serological tests provide an indication of infection, it may be necessary to consider all those who test seropositive as in fact, being infected. Further, certain of those individuals who are found to be seronegative may in fact be treated as being infected if certain other indications of infection, such as contact with a known carrier, are satisfied. While the terms "seropositive" and "seronegative" may be used herein as the most readily available indicators of infection, they are intended to be synonymous with "infected" or "non-infected" respectively.

Figure 1:
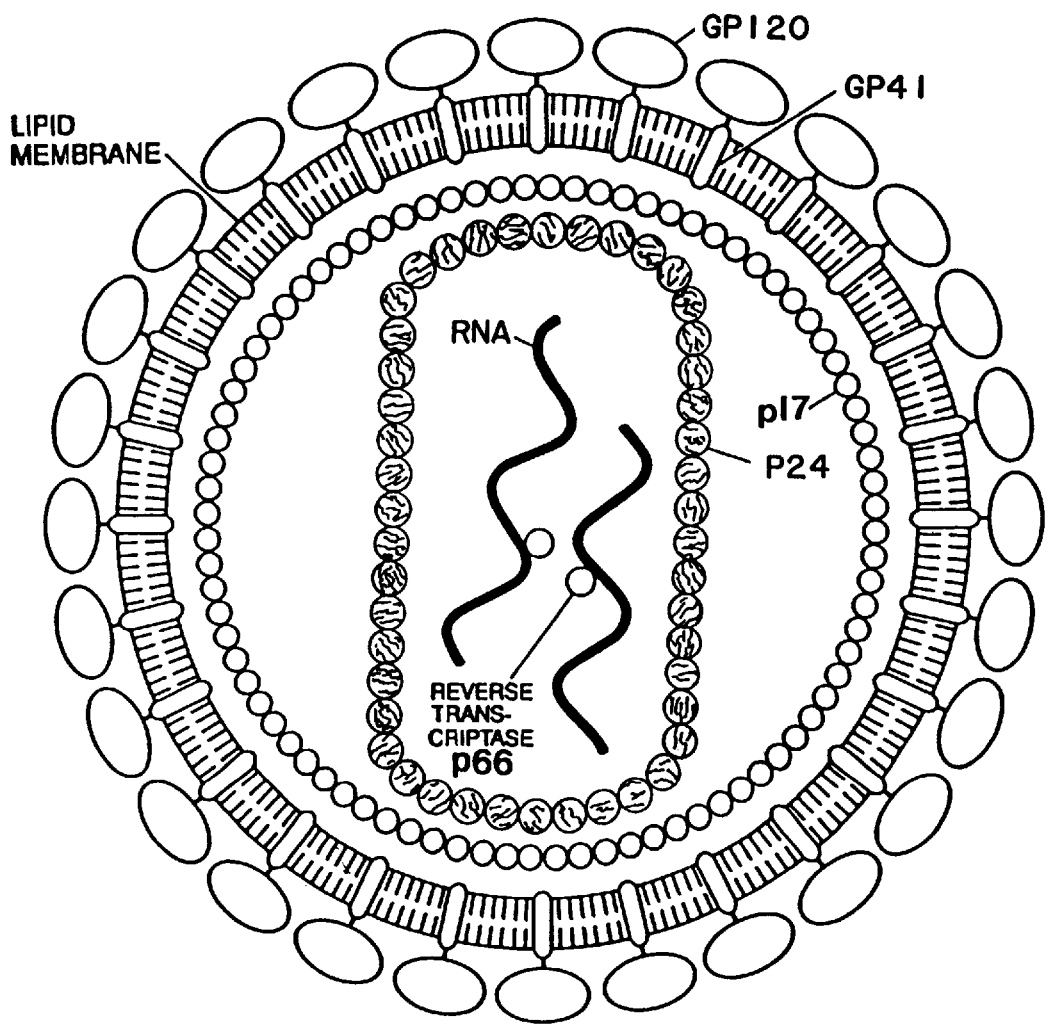
FIG. 1 is a schematic diagram of HIV showing arrangement of the various gene products.
Figure 2:
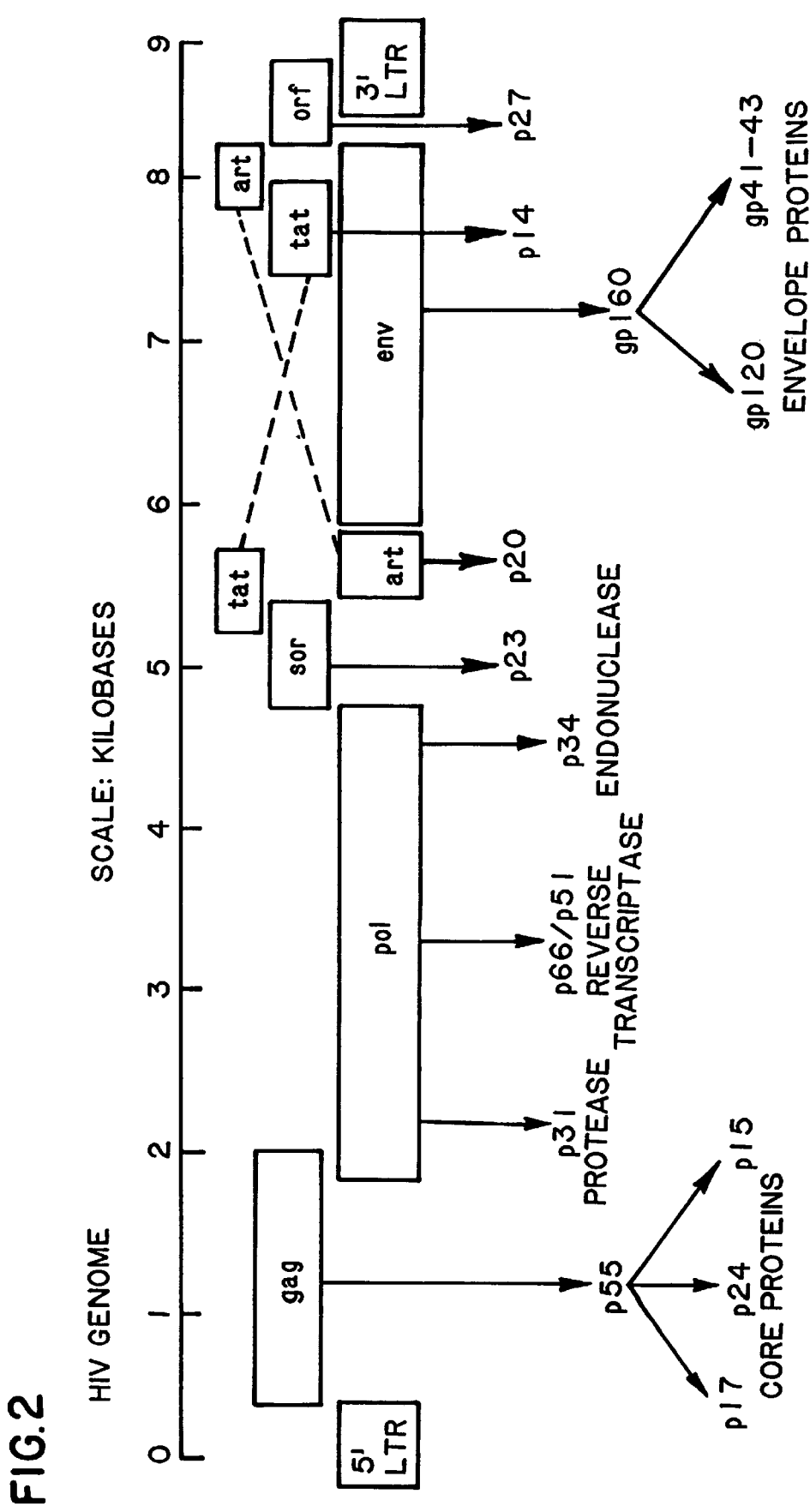
FIG. 2 is a diagram of the genes of HIV and the gene products coded therein.

Identification of HIV specific genes and gene products is based on the terminology of HIV type 1 as presented in FIG. 1. It is intended, however, that a reference to a specific gene or gene product of HIV type 1, based on its molecular weight, will also include the corresponding gene or gene product of HIV type 2, and, where an homologous gene is present, of other retroviruses. The gene products of other types and species may have slightly different molecular weights. For example, HIV type 1 gp41 is equivalent to gp36 of type 2, while type 1 gp120 corresponds to type 2 gp130. Genes are identified by italicized lower case designations, such as gag, while the corresponding gene product is identified by an upper case designation, such as GAG. The entire HIV gene has been sequenced. See Ratner et al. Nature 313:277(1985), which is incorporated herein be reference.

HIV can be cultured from a specimen of peripheral blood of infected individuals. For example, mononuclear cells from peripheral blood such as lymphocytes, can be obtained by layering a specimen of heparinized venous blood over a Ficoll-Hypaque density gradient and centrifuging the specimen. The mononuclear cells are then collected, activated, as with phytohemagglutinin for two to three days, and cultured in an appropriate medium, preferably supplemented with interleukin 2. The virus can be detected either by an assay for reverse transcriptase, by an antigen capture assay for p24, by immunofluorescence or by electron microscopy to detect the presence of viral particles in cells all of which are methods well-known to those skilled in the art. Once isolated, the virus can be transmitted to other cells.

It is important to use a non-infectious vaccine in order to avoid introducing the infection into a host. Various methods are well known for rendering a pathogen non-infectious. See for example Hanson, MEDICAL VIROLOGY II (1983) (de la Maza and Peterson, eds) Elsevier, N.Y. The virus may be inactivated or made replication-defective. Preferably, however, it is treated with a combination of beta-propiolactone and gamma radiation. For the amounts used herein, the beta-propiolactone must be in contact with the virus for a minimum of 2.5 hours. In order to completely eliminate any residual beta-propiolactone, the beta-propiolactone must remain in solution for a minimum of five hours at 37° C.

The isolated virus is then treated so as to remove the outer envelope proteins. Such removal is preferably accomplished by repeated freezing and thawing of the virus in conjunction with physical methods which cause the swelling and contraction of the viral particles, although other physical or non-physical methods, such as sonication, can also be employed alone or in combination.

Alternatively, substantially purified gene products of retrovirus such as HIV, other than the outer envelope proteins can be used as an immunogen. Such gene products include those products encoded by the gag genes (p55, p39, p24, p17 and p15), the nol genes (p66/psi and p31–34) and the transmembrane glycoprotein gp41. These gene products may be used alone or in combination. Alternatively, the gene products of the remaining five genes of the HIV genome may be used. The gene products may be isolated and purified from the virus or may be produced by cloning and expressing the appropriate gene in a host organism such as bacterial, fungal or mammalian cells, by methods well known in the art. Alternatively, the antigens may be synthesized, using methods well known in the art, such as automated peptide synthesis. The amino acid sequence of the gene products has been deduced from the nucleotide sequence.

A subset of individuals determined to have retroviral infections, such as HIV, can be effectively treated by active immunotherapy using a non-infectious immunogen prepared from the retrovirus. Animals known to have a retroviral infection can also be treated by such a method. In the case of HIV, a seropositive individual is immunized with an outer envelope free immunogen, preferably incorporated in an adjuvant. Alternatively, the immunogen can be administered in its aqueous form without an adjuvant. The dose is selected so as to be immunologically effective, and is generally between about 1 to 100 ug of protein, preferably about 30 ug of protein.

Active immunization is implemented and preferably repeated once at a minimum interval of at least 90 days, although additional boosts may be appropriate according to changes in the immunocompetence level, based, for example, on a decline in antibodies to HIV gene products other than outer envelope proteins. Such immunization is preferably accomplished initially by intramuscular injection followed by intradermal injection, although any combination of intradermal and intramuscular injections may be used.

Preferably, the immunoresponsiveness or immunocompetence of the seropositive individual is determined prior to immunization in order to determine an appropriate course of therapy. As a method of such determination, individuals' sera are screened for the presence of antibodies to p24 (as by means of ELISA), for RTI antibody and/or for the level of $T_4$ cells by methods well known in the art. Individuals exhibiting indicators of low immunocompetence, such as low p24 or RTI antibody titers or low numbers of $T_4$ cells, are appropriate candidates for passive immunotherapy, preferably in conjunction with, and either preceding or concomitant with, active immunotherapy.

Seronegative individuals can be vaccinated in order to induce immunoprotective factors to prevent infection. Preferably, the vaccine is administered initially by intramuscular injection followed by a booster injection given either intramuscularly or intradermally. A physiologically effective dose, preferably in the range of 1 to 100 ug and more preferably about 30 ug of immunogen is provided per dose. Preferably the vaccine is administered in conjunction with an adjuvant, most preferably a water-in-oil type adjuvant. Various appropriate adjuvants are well known in the art as reviewed by Warren and Chedid, CRC Critical Reviews in Immunology 8:83 (1988), which is incorporated herein by reference.

In addition, because antibodies to gp160/120 may facilitate virus absorption to cells, these specific antibodies can be removed from a person infected with HIV prior to immunotherapy. Immunosorbent columns composed of hollow cellulose fibers are modified to covalently link ligands reactive with anti-gp160/120 antibodies. Such ligands include gp160/120 antigens prepared from purified glycoproteins obtained from freshly harvested virus particles or from culture supernatant of HIV producing $T_4$ lymphocytes. Alternatively, such ligands can be produced by recombinant DNA methods using transfected cells. Alternatively, anti-idiotypes reactive with anti-gp160/120 antibodies may be used. Such anti-idiotype antibodies can be made by methods well known in the art, for example, Riott et al. Lancet, May 9, 1981, p. 1041 et seq. which is incorporated herein by reference. Methods of utilizing such columns for the extracorporeal removal of elicited antibodies are those described in Larue et al., Symp. on Plasma Exchange in Nephrology; Int'l. J. of Art. Organs 8:23 (1984), which is incorporated herein be reference.

B. Examples

The following examples are intended to illustrate but not limit the invention. While they are typical of those that might be used, other alternative procedures known to those skilled in the art may be alternatively employed.

EXAMPLE I

Preparation Of The Outer-Envelope Free Viral Particles

Cells infected with HIV, were grown in Media A consisting of RPMI 1640 with 10% fetal bovine serum (FBS) 25 mM HEPES, 50 ug/mL gentamicin and 100 ug/mL streptomycin.

The cultures were expanded by adding stock cells to spinner flasks and bringing the volume up to approximately 8 L with prewarmed Media A. The split ratio was approximately 1:5. A second split was performed as before with a split ratio of 1:3.

The supernatant from 5 to 7 day old suspension of the HIV infected cells was filtered through a 0.45 micron filter (Prostack; Millipore Corporation, Bedford, Mass.). A 1:40 stock solution of beta-propiolactone (Sigma Chemical Corporation, St. Louis, Mo.) was prepared fresh prior to use and added to the supernatant to a final concentration of 1:4000. The solution was incubated for five hours at 37° C. and the pH maintained at 7.2–7.4.

After 5 hours, 20 mL of the supernatant solution was removed in order to ascertain the level of infectivity and the amount of remaining beta-propiolactone. The supernatant was then frozen at −70° C. The frozen supernatant was then exposed to 4.5 mR $^{60}$Cobalt gamma irradiation (Radiation Sterilizers Inc, Tustin, Calif.).

The supernatant solution was then thawed and concentrated 40× using the Millipore Pellicon system with 100,000 MW cutoff polysulfone filters, following the instructions provided by the manufacturer. The concentrate was place in T-21 rotor bottles (Beckman Instruments, Brea, Calif.) previously treated with 70% isopropyl alcohol (IPA) and centrifuged at 28,000 rpm for one hour. The supernatant from the tubes was removed and the pellets resuspended in Sodium Tris EDTA (NTE) to a final volume of approximately 24 mL NTE. Four mL of this suspension was layered over 8 ml 30% sucrose in polyallomer tubes that have been previously treated with 70% IPA and centrifuged for one hour at 28,000 rpm. The supernatant was drained from the 30% sucrose and the pellets thoroughly resuspended in NTE.

A gradient in ultraclear centrifuge tubes previously treated with 70% IPA was established by adding 3 mL 45% sucrose to the tube and overlayering 6 ml 30% sucrose. Three mL of the above suspension were layered thereon. The tubes were centrifuged for 60 minutes at 28,000 rpm.

The solution above bands at the 35% interface was pipetted off and discarded. The bands from all tubes were combined in one conical tube and diluted 1:10 with phosphate buffered saline (PBS). The solution was centrifuged in polyallomer tubes pretreated with 70% IPA for one hour at 28,000 rpm. The supernatant was removed and the pellets resuspended in PBS at a concentration 1 ml per 10 L starting material.

Alternatively, particularly where the immunogen is prepared in large quantities, the irradiation step can be performed after the bands were combined. Thereafter, the virus is banded on a 15–50% sucrose gradient. The virus bands were combined and resuspended in PBS. The virus was pelleted at 23,000 RPM for 1 hour and resuspended in PBS to a final concentration of 1.0 mg/mL.

The amount of protein present was determined according to the method of Bradford, Anal. Biochem. 72:248 (1976), which is incorporated herein by reference. The protein was diluted to a final concentration of 1.0 mg/ml in PBS.

The level of residual B-propiolactone in the immunogen prepared by the method of Example I was determined using a capillary gas liquid chromatograph (Carlo ERBA Series 4100), according to the manufacturer's instructions. Standard solutions of B-propiolactone and butyric acid having concentrations between 1 ppm and 500 ppm were prepared. Two uL samples were injected into the capillary chromatograph using the instructions provided by the manufacturer. The detection limit was determined to be 0.1 ppm. The immunogen was determined to contain less than 0.05 ppm B-propiolactone.

Eight samples of immunogen prepared according to the protocol above were analyzed for beta-propiolactone content by capillary gas chromatography, using butyric acid as an internal standard. The chromatographic condition were as follows: column: 30 m×0.25 mm fused silica open tubular; stationary phase: 100% cyanopropyl silicone; injector temperature 140° C.; Temperature program 70° C./1 minute, 20° C./minute to 130° C.; Injection technique: splitless. Under the above conditions, the retention times of beta-propiolactone and butyric acid were 7.52 minutes and 6.70 minutes, respectively. An injection of 2 uL of a 1 ppm solution of beta-propiolactone produced a peak which could be quantitated. Concentration of the 1 ppm solution to one tenth of its volume by solvent evaporation at 40° C. under reduced pressure did not cause an appreciable loss of beta-propiolactone. The detection limit after concentration was 0.1 ppm (0.1 ug/mi).

Figure 4:
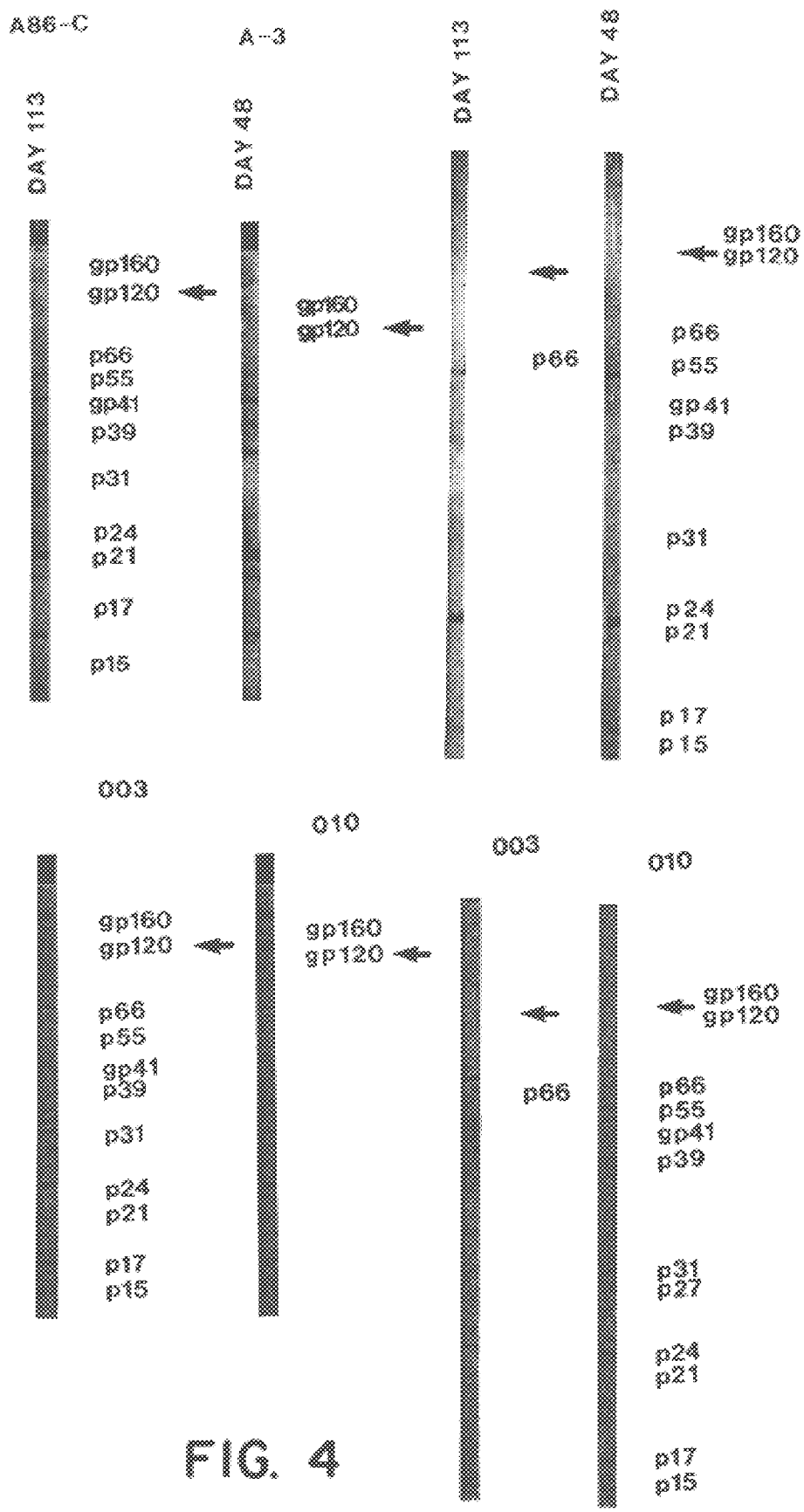
FIG. 4 shows Western Blots of the immunogen showing that it is free of outer envelope proteins when screened with homologous and heterologous sera that contain high titers of antibody to the outer envelope proteins.

In order to confirm that the immunogen was free of the outer envelope proteins, the immunogen was first separated on 11.0% SDS-PAGE gels according to the method of Laemmli, U.K., Nature 227:680 (1970), which is incorporated herein by reference. The separated material was then transferred to nitrocellulose paper according to the method of Towbin et al., Proc. Natl. Acad. Sci. 76:4350 (1979), which is incorporated herein by reference, and immunostained according to the method of Tsang et al., Meth. Enzymology 92:377 (1983), which is incorporated herein by reference. As can be seen in FIG. 4, the western blots of the immunogen so obtained do not have a band corresponding to gp120/160, as indicated in the controls when reacted with sera containing high titers of anti-gp160/120.

As shown in FIG. 4, commercial Western Blot strips having HIV proteins thereon (Bio-Rad, Richmond, Calif.) ("Commercial western blot strips") screened with heterologous sera (chimpanzee A86-C and A-3) containing high titer antibodies to outer envelope proteins, gp160/120 were negative (non-reactive) on Western Blot strips prepared with the outer envelope free immunogen by the method of Example I. Homologous human sera (003 and 010) containing high titer antibodies to outer envelope proteins gp 160/120 were reactive with commercial Western Blot strips but were non-reactive on the Western Blot strips prepared from the outer envelope free immunogen. Both homologous and heterologous sera reacted with other HIV gene products.

The lack of outer envelope proteins on the immunogen particles was confirmed by electron microscopy. The immunogen preparation was fixed with 2.5% glutaraldehyde, post-fixed with $OsO_4$, dehydrated through a graded series of ethanol solutions and embedded in EPON-812. Thin sections were prepared with an LKB Microtome (LKB, Uppsala, Sweden) using a diamond knife. The thickness of the sections was 60 nm. Sections were stained with uranyl acetate and lead citrate and observed and photographed with a Zeiss 109 Electron Microscope. HIV infected cells were prepared by the same procedure as controls. The immunogen was seen to lack the darkly staining outer coat exhibited by the controls, which reflects gp160/120 on the viral surface.

EXAMPLE II

Immunotherapy of Seropositive Individuals

Nine individuals seropositive for HIV were treated by immunotherapy. An immunogen comprising non-infectious HIV particles devoid of the outer envelope proteins was prepared according to the method of Example I. The immunogen was emulsified in a 1 to 1 proportion in incomplete Freund's adjuvant (IFA) in an emulsifier (Spex 8000 Mixer Mill; Spex Industries Inc., Edison, N.J.). 1.0 mL of solution, containing 100 ug of protein, was administered intramuscularly. A booster of 100 ug of protein without adjuvant was administered 90 days later by intradermal injection.

The presence of HIV virus in a patient's peripheral blood lymphocytes was determined both pre- and post-immunization by cocultivation with freshly supplied peripheral blood lymphocytes stimulated with PHA and interleukin-2 (IL-2) by the method Gallo et al., J. Clin. Microb. 25:1291 (1987), which is incorporated herein by reference. Kits to detect the presence of HIV antigens, such as p24 are commercially available (for example, HIV p24 Assay; E. I. DuPont & DeNemours Co., Inc., Wilmington, Del.). Each patient was tested 3 times prior to immunization, and at weeks 2, 4, 6, 8, 12 and 14 post immunization.

Table I provides the results of viral isolation from the patients. Patients 010 and 003, from both of whom HIV had been isolated prior to immunization, failed to exhibit isolatable virus through week 12 post immunization. Patients 008 and 009 were virus free by culture through week 8 post immunization. All four of these patients had exhibited high titers of anti-p24 (i.e., referring to the group specific core protein p24) antibody (>1:5000) and RTI i.e., anti-reverse transcriptase (antibody to reverse transcriptase) (>1:1000) before immunization. The remaining five patients, who exhibited lower anti-p24 and RTI titers prior to immunization, continued to exhibit isolatable virus after immunization.

Although the invention has been described with reference to the presently-preferred embodiment, it should be understood that various modifications can be made without departing from the spirit of the invention. Accordingly, the invention is limited only by the following claims.

a) selecting an immunocompetent individual having a retroviral infection; and b) recovering anti-retroviral antibodies produced by said individual.

4. Purified and isolated anti-retroviral antibodies obtained by the method of claim 3.

5. A method of obtaining anti-HIV antibodies, comprising the steps of:

a) selecting an immunocompetent individual having an HIV infection; and b) recovering anti-HIV antibodies produced by said individual.

6. Purified and isolated anti-HIV antibodies obtained by the method of claim 5.

7. A method of producing anti-retroviral antibodies, comprising the steps of:

a) immunizing a mammal with an immunogen comprising two or more retroviral proteins, provided that none of said retroviral proteins is an outer envelope protein, whereby said immunization stimulates production of anti-retroviral antibodies; and b) recovering the anti-retroviral antibodies produced by said mammal.

8. Purified and isolated anti-retroviral antibodies produced by the method of claim 7.

9. An immunogen comprising a non-infectious intact retrovirus devoid of outer envelope proteins.

10. The immunogen of claim 9, wherein said retrovirus is rendered non-infectious by treatment with gamma radiation and beta-propriolactone.

11. A composition comprising the immunogen of claim 9 together with an adjuvant.

TABLE I

IMMUNOLOGIC AND VIROLOGIC PROFILES IN SEROPOSITIVE VIREMIC ARC PATIENTS PRE- AND POST-IMMUNIZATION

| | Cytologic | | | | | Virologic | | | | | | |
|---|---|---|---|---|---|---|---|---|---|---|---|---|
| | T-4 | | Immunologic | | | | | | Post (wks) | | | |
| Patient | Pre | Post | Anti-p24 | RTI | N.A. | Pre | 2 | 4 | 6 | 8 | 12 | 14 |
| 003 | 518 | 671 | 250,000 | 2,560 | 40 | + − − | − | − | − | − | − | − |
| 010 | 229 | 297 | 500,000 | 10,240 | 80 | + + − | − | − | − | − | − | |
| 008 | 288 | 371 | 16,000 | 2,560 | 80 | − + − | − | − | − | − | + | |
| 009 | 219 | 261 | 8,000 | 2,560 | 80 | − + − | − | − | − | − | + | |
| 006 | 296 | 283 | 3,200 | 640 | 40 | + − + | + | + | + | − | − | + |
| 001 | 237 | 198 | 3,200 | 20 | 40 | + + + | − | − | + | − | + | |
| 004 | 261 | 277 | 400 | <20 | 20 | − − + | − | + | − | + | + | |
| 007 | 180 | 259 | 200 | 80 | 10 | + + + | + | + | − | + | + | |
| 005 | 228 | 98 | 170 | <20 | 14 | − − + | + | + | + | + | + | + |

N.A. refers to neutralizing antibody.

We claim:

1. A method of producing anti-HIV antibodies, comprising the steps of:

a) immunizing a mammal with an immunogen comprising two or more HIV proteins, provided that none of said HIV proteins is an outer envelope protein, whereby said immunization stimulates production of anti-HIV antibodies; and b) recovering the anti-HIV antibodies produced by said mammal.

2. Purified and isolated anti-HIV antibodies produced by the method of claim 1.

3. A method of obtaining anti-retroviral antibodies, comprising the steps of:

12. A method of preparing the immunogen of claim 9, comprising the steps of:

a. growing intact retrovirus in culture; and b. removing the outer envelope proteins from said intact retrovirus.

13. A method of producing antibodies useful for the treatment of retroviral infections, comprising the steps of:

a. immunizing a mammal with the immunogen of claim 9; and b. recovering the antibodies produced by said mammal.

14. Isolated antibodies produced by the method of claim 13.

* * * * *

UNITED STATES PATENT AND TRADEMARK OFFICE
CERTIFICATE OF CORRECTION

PATENT NO. : 5,885,578
DATED : March 23, 1999
INVENTOR(S) : Salk et al.

It is certified that error appears in the above-identified patent and that said Letters Patent is hereby corrected as shown below:

Column 2,
Line 66, please delete "time" and replace therefor with -- times --.

Column 4,
Line 23, please delete "Sunra." and replace therefor with -- Supra. --.

Column 5,
Line 44, please delete "nol" and replace therefor with -- pol --.
Line 44, please delete "/psi" and replace therefor with -- /p51 --.
Line 66, in both instances please delete "ug" and replace therefor with -- µg --.

Column 6,
Line 28, please delete "ug" and replace therefor with -- µg --.
Line 29, please delete "ug" and replace therefor with -- µg --.
Line 66, in both instances please "ug" and replace therefor with -- µg --.

Column 7,
Line 23, please delete "place" and replace therefor with -- placed --.
Line 51, please delete "23,000" and replace therefor with -- 28,000 --.
Line 63, please delete "uL" and replace therefor with -- µL --.

Column 8,
Line 4, please delete "condition" and replace therefor with -- conditions --.
Line 11, please delete "uL" and replace therefor with -- µL --.
Line 17, please delete "ug" and replace therefor with -- µg --.
Line 17, please delete "/mi" and replace therefor with -- /ml --.

UNITED STATES PATENT AND TRADEMARK OFFICE
CERTIFICATE OF CORRECTION

PATENT NO. : 5,885,578
DATED : March 23, 1999
INVENTOR(S) : Salk et al.

It is certified that error appears in the above-identified patent and that said Letters Patent is hereby corrected as shown below:

Column 9,
Line 1, please delete "ug" and replace therefor with -- µg --.
Line 2, please delete "ug" and replace therefor with -- µg --.

Signed and Sealed this

Twenty-fifth Day of September, 2001

*Attest:*

*Attesting Officer*

NICHOLAS P. GODICI
*Acting Director of the United States Patent and Trademark Office*